United States Patent
Faizan et al.

(10) Patent No.: US 11,766,549 B2
(45) Date of Patent: Sep. 26, 2023

(54) WEARABLE DEVICE FOR MANAGING ALCOHOL-DRIVEN VIOLENCE

(71) Applicant: Mirza Faizan, Irving, TX (US)

(72) Inventors: Mirza Faizan, Irving, TX (US); Reya Dawlah, Sherman, TX (US); Zad Ahmed, Carrollton, TX (US); Naadira Shareef Kateeb, Plano, TX (US); Tarik Syed, Dallas, TX (US); Rishi Kata, Allen, TX (US); Lingesh Veda, Irving, TX (US); Yusuf Zakiy Ali, Richardson, TX (US); Shreya Nair, Allen, TX (US); Ahmed Malik, Plano, TX (US); Mirza Rizwan, Patna (IN)

(*) Notice: Subject to any disclaimer, the term of this patent is extended or adjusted under 35 U.S.C. 154(b) by 193 days.

(21) Appl. No.: 17/403,484

(22) Filed: Aug. 16, 2021

(65) Prior Publication Data
US 2023/0048142 A1    Feb. 16, 2023

(51) Int. Cl.
*A61M 3/00* (2006.01)
*A61K 31/45* (2006.01)
*A61M 37/00* (2006.01)
*A61K 31/4515* (2006.01)

(52) U.S. Cl.
CPC ..... *A61M 37/0015* (2013.01); *A61K 31/4515* (2013.01); *A61M 2037/0023* (2013.01); *A61M 2037/0061* (2013.01); *A61M 2205/18* (2013.01); *A61M 2205/3303* (2013.01); *A61M 2205/3553* (2013.01); *A61M 2205/3606* (2013.01); *A61M 2205/82* (2013.01); *A61M 2209/088* (2013.01); *A61M 2230/60* (2013.01)

(58) Field of Classification Search
CPC ...... A61M 37/0015; A61M 2037/0023; A61M 2037/0061; A61M 2205/18; A61M 2205/3303; A61M 2205/3553; A61M 2205/3606; A61M 2205/82; A61M 2209/088; A61M 2230/60; A61K 31/4515
See application file for complete search history.

(56) References Cited

U.S. PATENT DOCUMENTS

2009/0099502 A1*  4/2009  Tokumoto ......... A61M 37/0015
                                                    604/21
2017/0095184 A1*  4/2017  Heikenfeld .......... A61B 5/4839

* cited by examiner

*Primary Examiner* — Amber R Stiles

(57) ABSTRACT

A wearable device 100 for managing alcohol-driven violence is disclosed. The device 100 comprises a capsule C1 adapted to sense sweat of wearer and detect a level of alcohol in the sweat, a capsule C3 adapted to convert a data detected by the capsule C1 to generate signal activating a capsule C4, a capsule C2 adapted to provide power to the capsule C3, and a capsule C5 adapted to detect a muscle activity of the wearer, wherein the capsule C4 is adapted to inject a drug into the body of the wearer, when activated, and wherein the capsule C5 alerts authorities when no muscle activity is detected.

9 Claims, 3 Drawing Sheets

WEARABLE DEVICE FOR MANAGING ALCOHOL-DRIVEN VIOLENCE

FIELD OF THE INVENTION

The present invention relates to a wearable device, and particularly, a wearable device for managing alcohol-driven violence by the person wearing said device.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

More than 1.4 million incidents of public drunk violence occur each year and more than ¼ of homicides occur due to alcoholism. Infact, the intake of alcohol is not good for health of the one consuming it. Apart from bad impact on the health in long run, consumption of alcohol often leads to numbness in the nervous system and the person loses control over himself. It may lead to unnecessary violence most of the times. It is seen that there are certain regulations in certain areas where intake of alcohol is strictly prohibited and anyone found violating such regulations is accordingly punished.

Currently in the market, wristbands are there only with the sweat sensor component that detects the alcohol level from your sweat and tracks it in a database. It measures the amount of alcohol in one's system. However, there are no other commercial methods that exist to specifically target the active prevention of drunk violence.

Therefore, there arises a need to provide a device, and preferably a wearable device, that can effectively detect the wearer's alcohol consumption and then distribute a mood stabilizer into their bloodstream, if necessary. Further, the device should also be adapted to prevent drunk violence.

OBJECTIVE OF THE INVENTION

The present disclosure is aimed at providing a wearable device that can effectively detect the wearer's alcohol consumption and then distribute a mood stabilizer into their bloodstream, if necessary.

Another object of the present invention is to provide a wearable device that can prevent alcohol driven violence.

Yet another object of the present invention is to provide a wearable device that can manage alcohol driven violence and is fairly cost effective.

Yet another object of the present invention is to provide the wearable device that can be used for individuals with a record of alcohol-driven violence, and can prevent the wearer from taking the device off without discretion.

SUMMARY OF THE INVENTION

This summary is provided to introduce a selection of concepts in a simplified format that are further described in the detailed description of the present disclosure. This summary is not intended to identify key or essential inventive concepts of the present disclosure, nor is it intended for determining the scope of the present disclosure.

According to an embodiment of the present disclosure, a wearable device for managing alcohol-driven violence is disclosed. The device comprisesa capsule C1 adapted to sense sweat of wearer and detect a level of alcohol in the sweat, a capsule C3 adapted to convert a data detected by the capsule C1 to generate signal activating a capsule C4, a capsule C2 adapted to provide power to the capsule C3, and a capsule C5 adapted to detect a muscle activity of the wearer, wherein the capsule C4 is adapted to inject a drug into the body of the wearer, when activated, and wherein the capsule C5 alerts authorities when no muscle activity is detected.

According to an embodiment, the wearable device is an armband.

According to an embodiment, the capsule C1 comprises one or more sweat sensors, and wherein the capsule C1 comprises an open back providing full access to the wearer's skin.

According to an embodiment, the capsule C2 comprises one or more matrix mercury thermoelectric energy converters for converting body heat of the wearer into energy.

According to an embodiment, the capsule C3 comprises a Raspberry Pi and a cooling system to prevent the raspberry from overheating.

According to an embodiment, the capsule C4 comprises a plastic ampoule of haloperidol, and opening with a microneedle patch.

According to an embodiment, the microneedle patch comprises a plurality of microtubes each attached onto a microneedle and merging into a single tube attached to the ampoule.

According to an embodiment, the microneedle patch is of 2 mL

According to an embodiment, the drug is a mood stabilizing drug.

According to an embodiment of the invention, a method of managing alcohol-driven violence by a wearer of a wearable device comprises steps of sensing and analyzing, by a sweat sensor, sweat of the wearer to produce a sweat data; translating, by a microcomputer, the sweat data to produce signals; transmitting the signals, by the microcomputer, to a drug delivery system; injecting, by the drug delivery system, a drug into the body of the wearer; detecting, by a muscle activity detector, the muscle activity of the wearer; and alarming authorities, by the device, in case of no detection of the muscle activity.

BRIEF DESCRIPTION OF DRAWINGS

To further clarify the advantages and features of the present disclosure, a more particular description of the disclosure will be rendered by reference to specific embodiments thereof, which is illustrated in the appended drawings. It is appreciated that these drawings depict only typical embodiments of the disclosure and are therefore not to be considered limiting of its scope. The disclosure will be described and explained with additional specificity and detail with the accompanying drawings.

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

Figure 1:
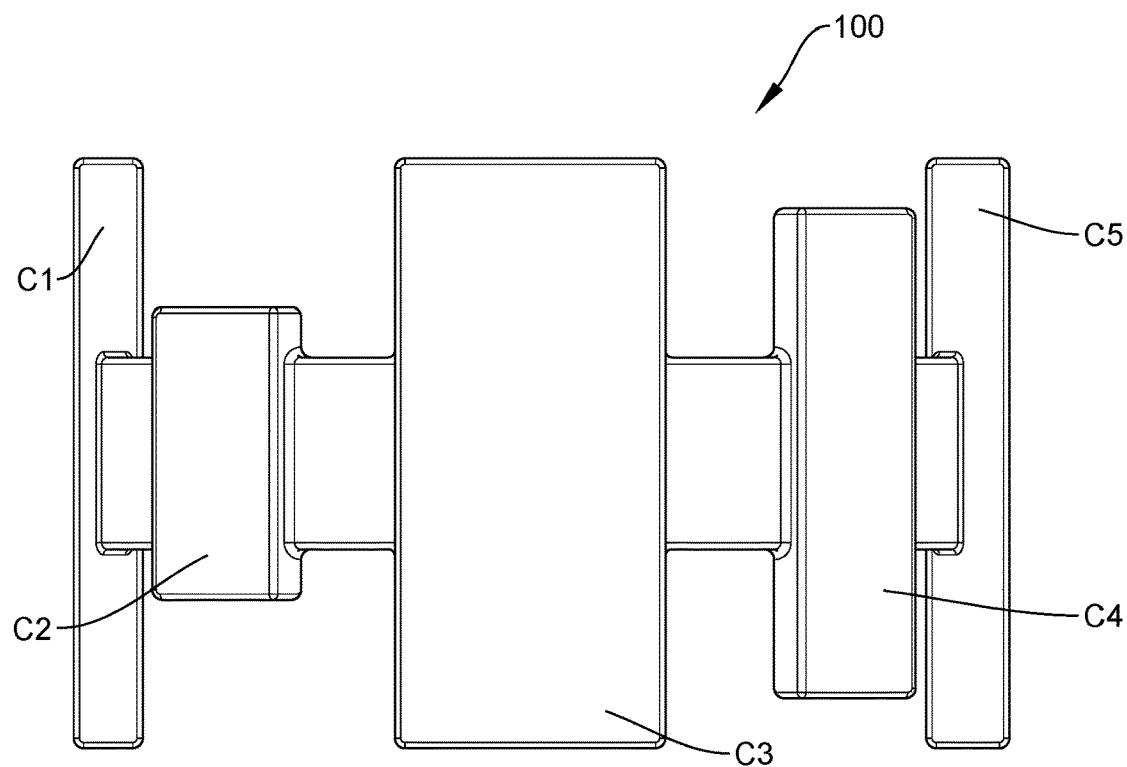
FIG. 1 and FIG. 1A illustrate views of the wearable device for managing alcohol-driven violence, according to an embodiment of the invention.

Further, skilled artisans will appreciate that elements in the drawings are illustrated for simplicity and may not have necessarily been drawn to scale. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION OF THE INVENTION

For the purpose of promoting an understanding of the principles of the invention, reference will now be made to the embodiment illustrated in the drawings, and specific language will be used to describe the same. It will nevertheless be understood that no limitation of the scope of the invention is thereby intended. Such alterations and further modifications in the illustrated system, and such further applications of the principles of the invention as illustrated therein would be contemplated as would normally occur to one skilled in the art to which the invention relates. Unless otherwise defined, all technical and scientific terms used herein have the same meaning as commonly understood by one of ordinary skilled in the art. The system, methods, and examples provided herein are illustrative only and are not intended to be limiting.

The term "some" as used herein is to be understood as "none or one or more than one or all." Accordingly, the terms "none," "one," "more than one," "more than one, but not all" or "all" would all fall under the definition of "some." The term "some embodiments" may refer to no embodiments or to one embodiment or to several embodiments or to all embodiments, without departing from the scope of the present disclosure.

The terminology and structure employed herein is for describing, teaching, and illuminating some embodiments and their specific features. It does not in any way limit, restrict or reduce the spirit and scope of the claims or their equivalents.

More specifically, any terms used herein such as but not limited to "includes," "comprises," "has," "consists," and grammatical variants thereof do not specify an exact limitation or restriction and certainly do not exclude the possible addition of one or more features or elements, unless otherwise stated, and furthermore must not be taken to exclude the possible removal of one or more of the listed features and elements, unless otherwise stated with the limiting language "must comprise" or "needs to include."

Whether or not a certain feature or element was limited to being used only once, either way, it may still be referred to as "one or more features" or "one or more elements" or "at least one feature" or "at least one element." Furthermore, the use of the terms "one or more" or "at least one" feature or element do not preclude there being none of that feature or element, unless otherwise specified by limiting language such as "there needs to be one or more . . . " or "one or more element is required."

Unless otherwise defined, all terms, and especially any technical and/or scientific terms, used herein may be taken to have the same meaning as commonly understood by one having ordinary skills in the art.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfill the requirements of uniqueness, utility and non-obviousness.

Use of the phrases and/or terms including, but not limited to, "a first embodiment," "a further embodiment," "an alternate embodiment," "one embodiment," "an embodiment," "multiple embodiments," "some embodiments," "other embodiments," "further embodiment", "furthermore embodiment", "additional embodiment" or variants thereof do not necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or alternatively in the context of more than one embodiment, or further alternatively in the context of all embodiments, the features and/or elements may instead be provided separately or in any appropriate combination or not at all. Conversely, any features and/or elements described in the context of separate embodiments may alternatively be realized as existing together in the context of a single embodiment.

Any particular and all details set forth herein are used in the context of some embodiments and therefore should not be necessarily taken as limiting factors to the attached claims. The attached claims and their legal equivalents can be realized in the context of embodiments other than the ones used as illustrative examples in the description below. Embodiments of the present invention will be described below in detail with reference to the accompanying drawings.

The present invention provides a wearable device 100 (hereinafter interchangeably referred to as "device" 100 or "armband" 100) that may be adapted to manage alcohol-driven violence. The wearable device 100 may be an armband 100 that may be worn around the arm of the wearer. In another embodiment, the wearable device 100 may be a band worn around the wrist of the wearer. In yet another embodiment, the wearable device 100 may be a chip or a like that may be kept in contact with the body of the wearer. The present description is being explained considering the first exemplary embodiment, i.e., the wearable device 100 may be an armband 100 worn around the arm of the wearer. The device 100 may be worn on either left or right arm of the wearer.

Figure 1A:
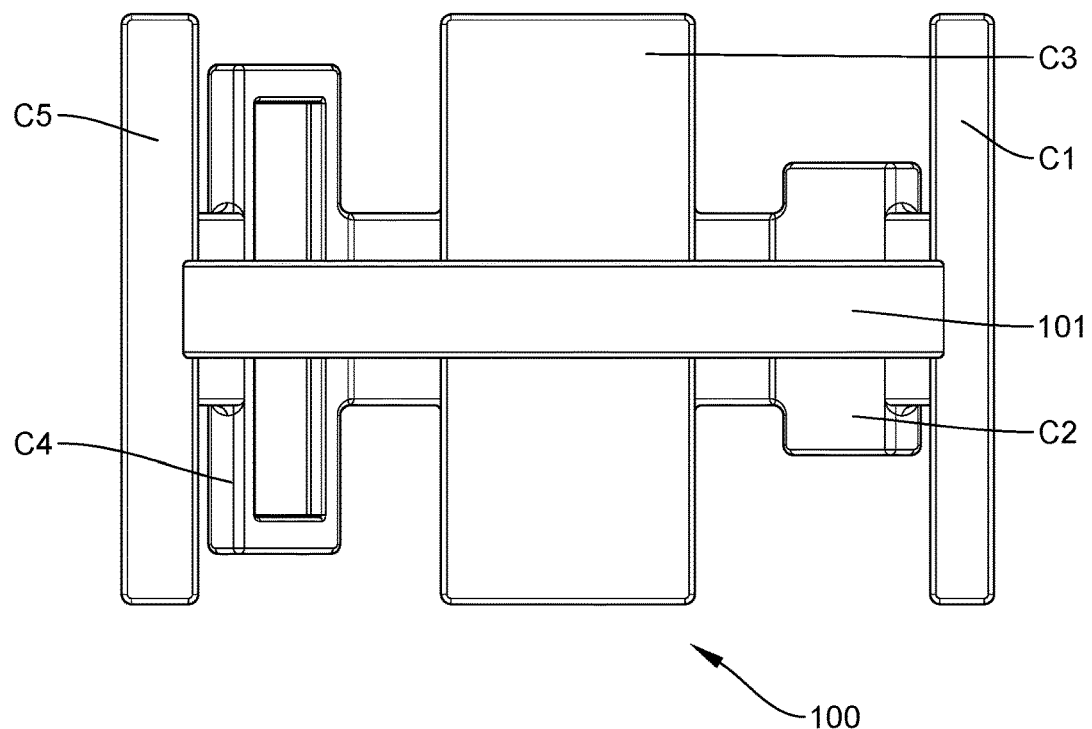

FIG. 1 illustrates view of the wearable device 100, according to an embodiment of the invention while FIG. 1A illustrates view of the wearable device 100, according to an embodiment of the invention. As according to an embodiment, the wearable device 100 for managing alcohol-driven violence, according to an embodiment of the present invention. The device 100 may be circular in shape, rather band shaped with the element arranged around the circular shape of the device 100. The device 100 may comprise an outer portion and an inner portion. The outer portion may be the portion of the device 100 placed on the outer of the arm of the wearer and the inner portion may be the portion of the device 100 placed on the inner region of the arm that is close to the body of the wearer. Elements may be arranged on the outer periphery of the armband 100. The elements may be arranged in capsule configuration. Therefore, there may be more than one capsules arranged on the outer circumference of the armband 100, according to an embodiment. While the inner portion of the armband 100 may be left empty of capsules so as to ensure the comfort of the wearer. In other words, in an embodiment, there may be a strap 101 shaped band with capsules laced on the outer portion of the band while the inner portion of the band may remain empty.

Referring to FIG. 1, in an embodiment, the device 100 may comprise five capsules C1, C2, C3, C4, and C5 arranged on the outer portion of the band.

Further the wearable device 100 for managing alcohol-driven violence, according to an embodiment of the present invention. The device 100 may comprise a capsule (hereinafter C1) on one of a side of the device 100. The C1 may comprise one or more sweat sensor adapted to sense sweat of the wearer.

As according to an embodiment of the invention, the structure of sweat sensor arranged in the device 100. The said capsule C1 may have an open back, i.e., there may be no cover at the back of the capsule. Since, the C1 may have an open back, the sensor may full access to the wearer's skin. Therefore, the sensor may cause optimal sweat generation and analysis. Particularly, the sensor may analyze the level of ethanol in the sweat of the wearer. The wearer may wear the device 100 on arm and whenever he sweats, the sweat sensor may sense the sweat and analyze it.

The device 100 may comprise a matrix mercury thermoelectric energy converter in a capsule (hereinafter C2) arranged at one of a side of a middle capsule. In an embodiment, the C2 may comprise around five matrix mercury thermoelectric energy converters that may be boost converters. The matrix mercury thermoelectric energy converters may be ideal for harvesting and managing surplus energy form extremely low input voltage sources. The energy converters may be designed for converting thermal energy between small temperature gradients into useful electrical output.

The device 100 may further comprise a raspberry pi and corresponding cooling system in a middle capsule (hereinafter C3). In an embodiment, the device 100 may be centered around the Raspberry Pi. Further, a Raspberry Pi zero structure and Raspberry Pi cooling system are used in the device 100. The Raspberry Pi may provide a set of General Purpose Input/Output pins, allowing control of electronic components in the device 100 for either physical computing and/or exploring the Internet of Things (I). The Raspberry Pi cooling system may be a fan for cooling the system by eliminating the heat produced by the electronic circuit of the Raspberry Pi. The Matrix mercury generator may convert body heat of the wearer into energy, providing an endless supply of power to the Raspberry Pi. The fan of the cooling system may be provided to prevent the Raspberry Pi from overheating, thereby preventing malfunctioning of the device 100 and increasing the working life of it. The Raspberry Pi may analyze the data of the C1 and translate it into a signal of release of mood stabilizer by another capsule.

Figure 2:
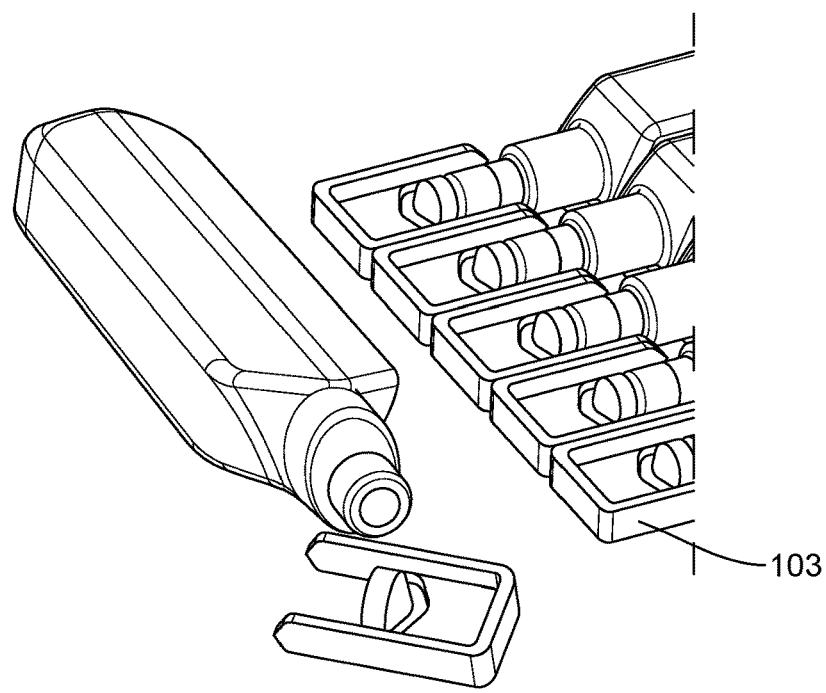
FIGS. 2, 3, and 4 illustrate main components of the wearable device for managing alcohol-driven violence, according to an embodiment of the present invention.
Figure 3:
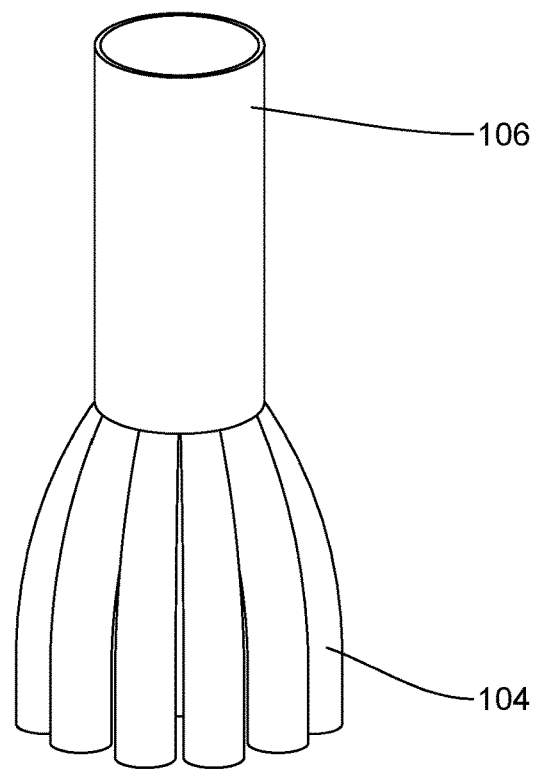

Referring to the figure, the device 100 may further comprise a capsule (hereinafter C4), connected to the C3, at of the ends of the device 100, that may be meant for plastic ampoule with haloperidol 103 and a drug delivery system. FIG. 2 illustrates the structure of elastic Ampule of Haloperidol 103 and FIG. 3 illustrates the structure of the drug delivery system in C3. As illustrated in the Figure, there may be several microtubes 104 that attach onto each microneedle 106 and then merge into a single tube that may be attached to the ampoule, thereby effectively feeding the drug into the microneedles 106. The structure has been explained in the FIG. 3, however, the figure is not to be considered to the exact scale, as the dimensions may vary from an embodiment to another embodiment.

Figure 4:
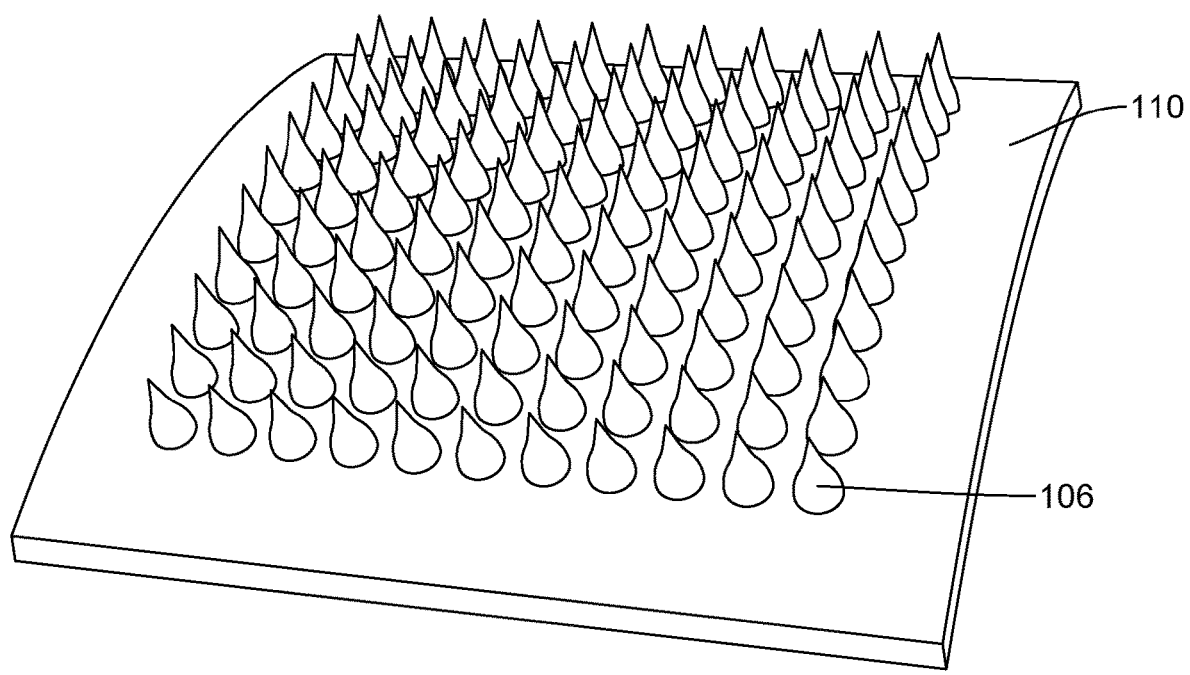

There may be an opening in the C4. The opening may have a microneedle patch 110 (structure illustrated in FIG. 4) wherein a microneedle 106 may be arranged. The microneedle 106 may descend into the wearer's skin and may inject drug into the wearer's body. In an embodiment, the C4 may comprise a 2 mL of drug patch wherein the drug may be a mood stabilizing drug to stabilize the mood of the wearer if he/she is found to have consumed alcohol.

Furthermore, the device 100 may comprise anther capsule (hereinafter C5) at one of the ends of the device 100. The C5 may comprise a muscle sensor component and may comprise an opening for an EMF electrode patch. The EMG-electrode patch may let an EMF electrode sense the wearer's muscle activity. Further the structure of EMG that may be round in an embodiment. There may be an opening in the C5 to let the electrode sense the muscle activity more accurately. The EMG muscle activity sensor may also be connected to the Raspberry Pi in order to detect the wearer's muscle activity or lack of it. In case the C5 does not detect any muscle activity or numbness, the device 100 senses that the individual is not wearing the armband 100. The device 100, then checks if the wearer has a history of alcohol consumption and/or violence. If the device 100 detects such history associated with the wearer, the device 100 sends an alert message to the concerned authorities, if the device 100 has been removed without permission. The concerned authorities may be doctor of the wearer, family, police or even rehab authorities depending on the embodiment. The manufacturer or the installer may set the concerned authorities.

A method of managing alcohol-driven violence may comprise sensing the sweat of the wearer by the one or more sweat sensors in the C1. The C1 may analyze the sweat of the wearer. In case, the wearer has consumed alcohol, ETG, which is a minor metabolite of alcohol, is formed in the liver of the wearer when alcohol reacts with glucuronic acid (substance that works to detoxify drugs by turning them into water-soluble compounds that are then removed from the body). The ETG may be sensed by the sweat sensor and the C1 may detect the level of ethanol in the body of the wearer. Since the sweat sensor is in continuous contact with the skin of the wearer, the sweat sensor senses and analyzes the sweat in real time. In case the level of ethanol is found in the sweat of the wearer, the C1 generates a data and shares it with another module, C3. The C3 translates the data into signals and sends the signals to the capsule C4 that has microneedle patch 110 to inject mood stabilizing drug into the body of the wearer. After injecting the drug into the body, the effect of alcohol on the nervous system minimizes and the chances of alcohol-driven violence is also reduced.

Another feature of the device 100 offers strict surveillance or control of the authorities over the wearer. The device 100 also monitors muscle activity of the wearer in real time by the muscle sensor in the C5. Wen no muscle activity is detected, the device 100 senses that the wearer has removed the armband 100. In such case, of the removal is without the permission of the concerned authorities, the C5 sends an alert to the authorities and inform that the band has been removed by the wearer.

In an embodiment, the device 100 also works when the wearer has not consumed alcohol. The muscle sensor may detect the muscle activity irrespective of the fact that alcohol is sensed in the sweat of the wearer. Depending on the quantum of the muscle activity detected, the muscle sensor may alarm the authorities if violence occurs, in an embodiment. In an embodiment, if alcohol is sensed in the sweat of the wearer, the muscle sensor may detect the quantum of violence. There may be a threshold set for the device 100 and if detected violence is more than the threshold, the device 100 may alarm the authorities.

The figures and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of the embodiments is by no means limited by these specific examples. Numerous variations, whether explicitly given in the specification or not, such as differences in structure, dimension, and use of material, are possible.

We claim:

1. A wearable device for managing alcohol-driven violence, the device comprising:
    a capsule C1 adapted to sense sweat of a wearer and detect a level of alcohol in the sweat;
    a capsule C3 adapted to convert data detected by the capsule C1 to generate a signal activating a capsule C4;
    a capsule C2 adapted to provide power to the capsule C3, wherein the capsule C2 comprises one or more matrix mercury thermoelectric energy converters for converting body heat of the wearer into energy; and
    a capsule C5 adapted to detect a muscle activity of the wearer,
    wherein the capsule C4 is adapted to inject a drug into a body of the wearer, when activated, and
    wherein the capsule C5 alerts authorities when no muscle activity is detected.

2. The wearable device as claimed in claim 1, wherein the wearable device is an armband.

3. The wearable device as claimed in claim 1, wherein the capsule C1 comprises one or more sweat sensors, and wherein the capsule C1 comprises an open back providing full access to the wearer's skin.

4. The wearable device as claimed in claim 1, wherein the capsule C3 comprises a Raspberry Pi and a cooling system to prevent the Raspberry Pi from overheating.

5. The wearable device as claimed in claim 1, wherein the capsule C4 comprises a plastic ampoule of haloperidol, and an opening with a microneedle patch.

6. The wearable device as claimed in claim 5, wherein the microneedle patch comprises a plurality of microtubes each attached onto a microneedle and merging into a single tube attached to the ampoule.

7. The wearable device as claimed in claim 6, wherein the microneedle patch is of comprises 2 mL of the drug.

8. The wearable device as claimed in claim 1, wherein the drug is a mood stabilizing drug.

9. A method of managing alcohol-driven violence by a wearer of a wearable device, the method comprising:
    sensing and analyzing, by a sweat sensor, sweat of the wearer to produce sweat data that includes a level of alcohol in the sweat;
    providing power, by converting body heat of the wearer into energy using one or more matrix mercury thermoelectric energy converters, to a microcomputer;
    translating, by the microcomputer, the sweat data to produce signals;
    transmitting the signals, by the microcomputer, to a drug delivery system;
    injecting, by the drug delivery system, a drug into a body of the wearer;
    detecting, by a muscle activity detector, a muscle activity of the wearer; and
    alarming authorities, by the device, in case of no detection of the muscle activity.

* * * * *